(12) United States Patent
Hofen et al.

(10) Patent No.: US 10,428,036 B2
(45) Date of Patent: Oct. 1, 2019

(54) PROCESS FOR THE EPOXIDATION OF PROPENE

(71) Applicants: EVONIK DEGUSSA GMBH, Essen (DE); THYSSENKRUPP INDUSTRIAL SOLUTIONS AG, Essen (DE)

(72) Inventors: Willi Hofen, Rodenbach (DE); Thomas Haas, Münster (DE); Wolfgang Wöll, Maintal (DE); Bärbel Kolbe, Witten (DE); Hans-Christian Dietz, Hattersheim (DE); Marc Brendel, Bruchköbel (DE); Bernd Jaeger, Bickenback (DE); Manfred Bärz, Freigericht (DE); Michael Kleiber, Hattersheim (DE)

(73) Assignees: Evonik Degussa GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 15/778,425

(22) PCT Filed: Nov. 25, 2016

(86) PCT No.: PCT/EP2016/078770
§ 371 (c)(1),
(2) Date: May 23, 2018

(87) PCT Pub. No.: WO2017/089516
PCT Pub. Date: Jun. 1, 2017

(65) Prior Publication Data
US 2018/0346432 A1   Dec. 6, 2018

(30) Foreign Application Priority Data
Nov. 26, 2015   (EP) .................................... 15196510

(51) Int. Cl.
*C07D 301/12* (2006.01)
*C07D 301/19* (2006.01)
(Continued)

(52) U.S. Cl.
CPC ............. *C07D 301/12* (2013.01); *B01D 3/14* (2013.01); *B01J 29/7049* (2013.01);
(Continued)

(58) Field of Classification Search
CPC .. C07D 301/12; C07D 301/32; B01J 29/7049; B01J 23/30; B01D 3/14; B01D 2257/80; B01D 2257/7022
(Continued)

(56) References Cited

U.S. PATENT DOCUMENTS 4,308,409 A   12/1981   Wu et al.
5,274,140 A   12/1993   Venturello et al.
(Continued)

FOREIGN PATENT DOCUMENTS

DE   195 07 584   9/1996
EP   0 100 119   2/1984
(Continued)

OTHER PUBLICATIONS

International Search Report for PCT/EP2016/078770 filed Nov. 25, 2016.
(Continued)

*Primary Examiner* — Taylor V Oh
(74) *Attorney, Agent, or Firm* — Law Office of: Michael A. Sanzo, LLC

(57) ABSTRACT

In a process for the epoxidation of propene, comprising the steps of reacting propene with hydrogen peroxide, separating propene oxide and a recovered propene stream from the reaction mixture, separating propane from all or a part of the recovered propene stream in a C3 splitter column, and
(Continued)

passing the overhead product stream of the C3 splitter column to the epoxidation step, a propane starting material with a propane fraction of from 0.002 to 0.10 is used, the epoxidation is operated to provide a propane fraction in the reaction mixture of from 0.05 to 0.20 and the C3 splitter column is operated to provide an overhead product stream which comprises a propane fraction of at least 0.04 in order to reduce the size and the energy consumption of the C3 splitter column.

16 Claims, 2 Drawing Sheets

(51) Int. Cl.
  *C07D 301/32* (2006.01)
  *B01D 3/14* (2006.01)
  *B01J 29/70* (2006.01)
  *B01J 23/30* (2006.01)
(52) U.S. Cl.
  CPC .... *C07D 301/32* (2013.01); *B01D 2257/7022* (2013.01); *B01D 2257/80* (2013.01); *B01J 23/30* (2013.01)
(58) Field of Classification Search
  USPC .................................................. 549/529, 531
  See application file for complete search history.

(56) References Cited

U.S. PATENT DOCUMENTS

| | | | |
|---|---|---|---|
| 5,591,875 | A | 1/1997 | Chang et al. |
| 5,599,956 | A | 2/1997 | Pujado et al. |
| 6,372,924 | B2 | 4/2002 | Thiele |
| 6,673,950 | B1 | 1/2004 | Teles et al. |
| 6,861,042 | B2 | 3/2005 | Korl et al. |
| 7,169,945 | B2 | 1/2007 | Haas et al. |
| 7,173,143 | B2 | 2/2007 | Bender et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,053,438 | B2 | 8/2018 | Bolz et al. |
| 10,053,440 | B2 | 8/2018 | Bolz et al. |
| 10,087,158 | B2 | 10/2018 | Stock et al. |
| 10,100,024 | B2 | 10/2018 | Stochniol et al. |
| 10,125,108 | B2 | 11/2018 | Jahn et al. |
| 10,214,471 | B2 | 2/2019 | Wiederhold et al. |
| 10,214,504 | B2 | 2/2019 | Brendel et al. |
| 2003/0040637 | A1 | 2/2003 | Hofen et al. |
| 2005/0245751 | A1 | 11/2005 | Bender et al. |
| 2006/0014970 | A1 | 1/2006 | Goebbel et al. |
| 2006/0058539 | A1* | 3/2006 | Babler ................ C07D 301/12 549/529 |
| 2007/0004926 | A1 | 1/2007 | Schindler et al. |
| 2012/0142950 | A1* | 6/2012 | Teles .................... C07D 301/12 549/531 |
| 2015/0007951 | A1 | 1/2015 | Dietz et al. |
| 2017/0210718 | A1 | 7/2017 | Stochinol et al. |
| 2018/0002299 | A1 | 1/2018 | Bolz et al. |
| 2018/0002300 | A1 | 1/2018 | Bolz et al. |
| 2018/0030010 | A1 | 2/2018 | Breitenbach et al. |
| 2018/0030011 | A1 | 2/2018 | Stock et al. |
| 2018/0030012 | A1 | 2/2018 | Stock et al. |
| 2018/0057473 | A1 | 3/2018 | Stock et al. |
| 2018/0134676 | A1 | 5/2018 | Jahn et al. |
| 2018/0346432 | A1 | 12/2018 | Hofen et al. |
| 2018/0354878 | A1 | 12/2018 | Wiederhold et al. |
| 2018/0354923 | A1 | 12/2018 | Pascaly et al. |
| 2018/0370934 | A1 | 12/2018 | Brendel et al. |
| 2019/0023673 | A1 | 1/2019 | Schmidt et al. |

FOREIGN PATENT DOCUMENTS

| | | |
|---|---|---|
| EP | 0 230 949 | 8/1987 |
| EP | 0 659 473 | 6/1995 |
| EP | 0 757 045 | 2/1997 |
| EP | 1 247 806 | 10/2002 |
| EP | 1 489 074 | 12/2004 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/141734 | 11/2008 |
| WO | WO 2011/063937 | 6/2011 |
| WO | WO 2016/016070 | 2/2016 |

OTHER PUBLICATIONS

Written Opinion of the International Searching Authority for PCT/EP2016/078770 filed Nov. 25, 2016.
International Preliminary Report on Patentability for PCT/EP2016/078770 filed Nov. 25, 2016
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).
Guojie, et al., "Factors Affecting Propylene Epoxidation Catalyzed by Reaction-Controlled Phase-Transfer Catalyst," *Chinese Journal of Catalysis* 26:1005-1010 (Nov. 2005).
Kaur, et al., "Poloxometalate-catalysed epoxidation of propylene with hydrogen peroxide: microemulsion versus biphasic process," *Catalysis Communications* 5(11): 709-713 (Nov. 2004).
Li, et al., "Influence of composition of heteropolyphophatotungstate catalyst on epoxidation of propylene," *Journal of Molecular Catalysis A: Chemical* 218(2):247-252 (Aug. 2004).
Luthra, et al., "Homogeneous phase transfer catalyst recovery and re-use using solvent resistant membranes," *Journal of Membrane Science* 201:65-75 (2002).
Venturello, et al., "A New, Effective Catalytic System for Epoxidation of Olefins by Hydrogen Peroxide under Phase-Transfer Conditions," *J. Org. Chem.* 483831-3833 (1983).
U.S. Appl. No. 15/329,626, filed Jan. 26, 2017, US-2017/0210718 A1, dated Jul. 27, 2017, Stochinol.
U.S. Appl. No. 15/570,167, filed Oct. 15, 2017, US-2018/0134676 A1, dated May 27, 2018, Jahn.
U.S. Appl. No. 15/778,318, filed May 23, 2018, Brendel.
U.S. Appl. No. 15/778,337, filed May 23, 2018, Pascaly.
U.S. Appl. No. 15/778,562, filed May 23, 2018, Wiederhold.
U.S. Appl. No. 16/070,873, filed Jul. 18, 2018, Schmidt.
Ullmanns Encylopedia of Industrial Chemistry, online edition 2013, entry "propene," DOI 10.1002/14356007.a22_211.pub3.
U.S. Appl. No. 16/086,309, filed Sep. 18, 2018, Wöll.
U.S. Appl. No. 16/302,099, filed Nov. 15, 2018, Wiederhold.

\* cited by examiner

PROCESS FOR THE EPOXIDATION OF PROPENE

CROSS REFERENCE TO RELATED APPLICATIONS

The present application is U.S. national stage of international application PCT/EP2016/078770, which had an international filing date of Nov. 25, 2016, and which was published on Jun. 1, 2017. Priority is claimed to European application EP 15196510.0, filed on Nov. 26, 2015.

FIELD OF THE INVENTION

The present invention relates to a process for the epoxidation of propene with hydrogen peroxide in which a propene starting material containing propane can be used efficiently.

BACKGROUND OF THE INVENTION

The epoxidation of propene with hydrogen peroxide in the presence of an epoxidation catalyst is usually carried out with a molar excess of propene relative to hydrogen peroxide in order to avoid hydrogen peroxide decomposition and to achieve high selectivities for propene oxide. Epoxidation of propene with a heterogeneous titanium silicalite catalyst is known from EP 0 100 119 A1. Epoxidation of propene with a homogeneous manganese catalyst is known from WO 2011/063937. Epoxidation of propene with a homogeneous tungstophosphate catalyst is known from U.S. Pat. No. 5,274,140.

For an efficient use of propene, non-reacted propene has to be recovered from the reaction mixture of the epoxidation reaction and recycled to the epoxidation reaction. Commercial propene grades usually contain propane as an impurity due to the manufacturing processes used for making propene. Since the epoxidation catalysts used for epoxidizing propene have little or no activity for oxidizing propane, the use of a propene grade containing propane in an epoxidation process with a propene recycle will lead to accumulation of propane in the process. Efficient recycling of propene then requires a separation of propane from propene and a purge of propane from the process.

WO 2005/103024 discloses the use of a conventional C3 splitter column for separating propane from a mixture of propene and propane recovered from an offgas from an epoxidation process before recycling the propene to the epoxidation. Such a conventional C3 splitter column has to be operated with a high reflux ratio which leads to a high energy consumption.

WO 2004/018088 discloses recovery of propene and propane from a gaseous propylene oxide process purge stream by absorption in liquid propane followed by separation in a C3 splitter column, providing an overhead vapor stream containing 31.2% by weight propene and 65.2% by weight propane which is recycled to propylene oxide production. However, due to the high propane content in the recycle stream this method leads to a high accumulation of propane in the process that requires considerably larger equipment for the epoxidation reaction and the reaction mixture workup and increases energy consumption in the reaction mixture workup.

Therefore, there is still a need for a process for the epoxidation of propene with hydrogen peroxide in which a propene starting material containing propane can be used and propane can be purged from the process with less equipment and energy consumption.

SUMMARY OF THE INVENTION

It has now been found that when operating the epoxidation to provide a propane fraction in the non-reacted propene of from 0.05 to 0.20 and recovering non-reacted propene in a C3 splitter column operated to provide a vapor at the column top with a propane fraction of at least 0.04, the extra expense for larger equipment for the epoxidation reaction and the reaction mixture workup and increased energy consumption in the reaction mixture workup is more than compensated by a reduced equipment size and energy consumption of the C3 splitter column when compared to a conventionally operated C3 splitter column.

Subject of the invention is therefore a process for the epoxidation of propene, comprising the steps
a) continuously reacting propene with hydrogen peroxide in the presence of an epoxidation catalyst, using propene in molar excess to hydrogen peroxide, to provide a reaction mixture comprising propene oxide, non-reacted propene and propane;
b) separating propene oxide and a recovered propene stream with a total content of propene and propane of more than 90% by weight from the reaction mixture obtained in step a);
c) feeding all or a part of said recovered propene stream to a C3 splitter column for separating propene and propane and withdrawing an overhead product stream depleted in propane with regard to said recovered propene stream and a bottoms product stream enriched in propane with regard to said recovered propene stream from said column; and
d) passing the overhead product stream obtained in step c) to step a);
wherein a propene starting material containing propane with a mass ratio of propane to the combined amount of propene and propane of from 0.002 to 0.10 is fed to the process for the epoxidation of propene; the reaction mixture provided in step a) comprises propane with a mass ratio of propane to the combined amount of propene and propane of from 0.05 to 0.20; and the overhead product stream withdrawn from the C3 splitter column comprises propane with a mass ratio of propane to the combined amount of propene and propane of at least 0.04.

BRIEF DESCRIPTION OF DRAWINGS

FIG. 1 shows an embodiment where the propene starting material is fed directly to reaction step a).

FIG. 2 shows an embodiment where the propene starting material is fed as liquid to a feed point less than 10 theoretical stages below the top of the C3 splitter column.

FIG. 3 shows an embodiment where the propene starting material is fed to a C3 rectifier column of step b).

DETAILED DESCRIPTION OF THE INVENTION

Figure 1:
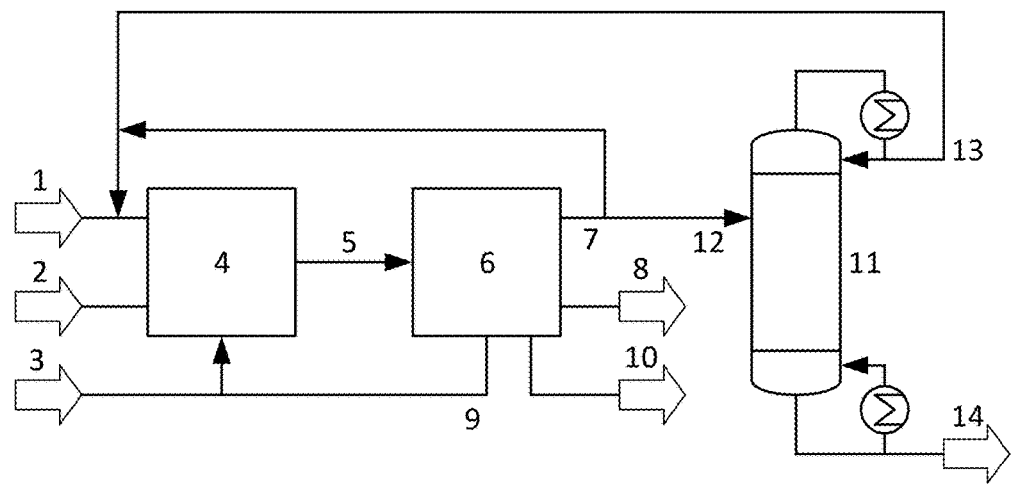
FIGS. 1 to 3 show preferred embodiments of the process of the invention.

The process of the invention uses a propene starting material which contains propane with a mass ratio of propane to the combined amount of propene and propane of from 0.002 to 0.10. The mass ratio is preferably from 0.003 to 0.08 and most preferably from 0.004 to 0.05. The propene starting material preferably contains less than 1% by weight of components other than propene and propane, more preferably less than 0.1% by weight. Suitable as propene starting material are commercial products of chemical grade propene and of polymer grade propene.

In step a) of the process of the invention, propene is continuously reacted in a reaction step with hydrogen peroxide in the presence of an epoxidation catalyst to provide a reaction mixture containing propene oxide, non-reacted propene and propane. Propene is used in excess to hydrogen peroxide, preferably with an initial molar ratio of propene to hydrogen peroxide of from 1.1:1 to 30:1, more preferably 2:1 to 10:1 and most preferably 3:1 to 5:1. Propene is preferably used in an excess sufficient to maintain an additional liquid phase rich in propene throughout step a). Using an excess of propene provides high reaction rate and hydrogen peroxide conversion and at the same time high selectivity for propene oxide.

Hydrogen peroxide can be used as an aqueous solution, preferably containing from 30 to 75% by weight hydrogen peroxide and most preferably from 40 to 70% by weight.

The epoxidation catalyst can be a homogeneous catalyst or a heterogeneous catalyst. Suitable homogeneous epoxidation catalysts are manganese complexes with polydentate nitrogen ligands, in particular 1,4,7-trimethyl-1,4,7-triazacyclononane ligands, as known from WO 2011/063937. Other suitable homogeneous epoxidation catalysts are heteropolytungstates and heteropolymolybdates, in particular polytungstophosphates, as known from U.S. Pat. No. 5,274,140, preferably quaternary ammonium salts of a polytungstophosphate. Suitable heterogeneous epoxidation catalysts are titanium zeolites containing titanium atoms on silicon lattice positions. Preferably, a titanium silicalite catalyst is used, preferably with an MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. For the shaping process the catalyst may contain 1 to 99% of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as fixed bed catalysts.

When the epoxidation catalyst is a titanium silicalite, the propene feed is preferably reacted with hydrogen peroxide in a methanol solvent to provide a liquid reaction mixture comprising methanol. The methanol solvent can be a technical grade methanol, a solvent stream recovered in the workup of the epoxidation reaction mixture or a mixture of both. The epoxidation reaction is then preferably carried out at a temperature of 30 to 80° C., more preferably at 40 to 60° C., and at a pressure of from 1.9 to 5.0 MPa, more preferably 2.1 to 3.6 MPa and most preferably 2.4 to 2.8 MPa. The epoxidation reaction is preferably carried out with addition of ammonia to improve propene oxide selectivity as described in EP 0 230 949 A2. Ammonia is preferably added in an amount of from 100 to 3000 ppm based on the weight of hydrogen peroxide. The epoxidation is preferably carried out in a fixed bed reactor by passing a mixture comprising propene, hydrogen peroxide and methanol over a fixed bed comprising a shaped titanium silicalite catalyst. The fixed bed reactor is preferably equipped with cooling means and cooled with a liquid cooling medium. Preferably, a cooled tube bundle reactor is used with the catalyst fixed bed arranged within the tubes and a temperature profile along the tube axis with temperatures within a range of less than 5° C. along at least 80% of the length of the catalyst fixed bed is maintained by cooling. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 h$^{-1}$, preferably 1.3 to 15 h$^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. The methanol solvent is preferably used in the epoxidation in a weight ratio of 0.5 to 20 relative to the amount of aqueous hydrogen peroxide solution. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions. Most preferably, the epoxidation reaction is carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827.

In step a) the propene is reacted in the presence of propane introduced into the process of the invention with the propene starting material. The amount of propane passed to step a) and the initial molar ratio of propene to hydrogen peroxide are chosen so that the reaction mixture provided in step a) comprises propane with a mass ratio of propane to the combined amount of propene and propane of from 0.05 to 0.20, preferably from 0.10 to 0.15.

In step b) of the process of the invention, propene oxide and a recovered propene stream are separated from the reaction mixture obtained in step a). The separation is carried out to provide a recovered propene stream with a total content of propene and propane of more than 90% by weight, preferably more than 95% by weight. The separation of propene oxide and of the recovered propene stream can be carried out by methods known from the art, such as by distillation. Separation step b) preferably comprises a step of separating propene with an overhead product in a C3 rectifier column from a bottoms product comprising propene oxide. Preferably, all or a part of the overhead product of the C3 rectifier column is withdrawn as recovered propene stream.

In step b) the reaction mixture is preferably subjected to a pressure reduction. Propene vapor formed by the pressure reduction may be recompressed and cooled to provide the recovered propene stream by condensation. Preferably, the propene vapor formed by the pressure reduction is recompressed and the compressed propene vapor is fed to a C3 rectifier column where it is separated to provide the recovered propene stream as the overhead product and a bottoms product comprising propene oxide and other components having a boiling point higher than propene, such as a solvent. The bottoms product can be combined with the liquid mixture remaining after the pressure reduction.

When methanol is used as solvent, the liquid mixture remaining after the pressure reduction is preferably separated by distillation in a pre-separation column to provide an overhead product comprising propene oxide, methanol and residual propene and a bottoms product comprising methanol, water and non-reacted hydrogen peroxide. The pre-separation column is preferably operated to provide an overhead product comprising from 20 to 60% of the methanol contained in the liquid phase of the last pressure reduction step. The pre-separation column preferably has from 5 to 20 theoretical separation stages in the stripping section and less than 3 theoretical separation stages in a rectifying section and is most preferably operated without reflux and without a rectifying section to minimize the residence time of propene oxide in the pre-separation column. The pre-separation column is preferably operated at a pressure of from 0.16 to 0.3 MPa. Propene oxide and methanol are condensed from the overhead product of the pre-separation column and propene is preferably stripped from the resulting condensate in a propene stripping column which provides a bottom stream comprising propene oxide and methanol which is essentially free of propene. Propene oxide is preferably separated from the bottoms stream of the propene stripping column in an extractive distillation using water as the extraction solvent. The extractive distillation is preferably operated with additional feeding of a reactive compound containing an unsubstituted $NH_2$ group and capable of reacting with acetaldehyde during the extractive distillation, as described in WO 2004/048335. Extractive distillation with a reactive compound provides a high purity propene oxide containing less than 50 ppm of carbonyl compounds.

In step c) of the process of the invention, all or a part of the recovered propene stream is fed to a C3 splitter column for separating propene and propane and an overhead product stream depleted in propane with regard to the recovered propene stream and a bottoms product stream enriched in propane with regard to the recovered propene stream are withdrawn from the column. The recovered propene stream is preferably fed to the C3 splitter column as a liquid to a feed point in the upper third of the C3 splitter column. The feed point is preferably less than 35 theoretical stages, more preferably less than 20 theoretical stages below the column top. When no other material is fed to the C3 splitter column, the recovered propene stream is preferably fed as a liquid at the uppermost stage of the column. The C3 splitter column may comprise discrete trays or column packings.

The C3 splitter column is operated to provide an overhead product stream which comprises propane with a mass ratio of propane to the combined amount of propene and propane of at least 0.04, preferably of from 0.04 to 0.15, more preferably of from 0.05 to 0.12. The desired propane fraction in the overhead product stream may be achieved by adjusting the number of separation stages in the rectifying section between the feed point of the recovered propene stream and the column top and by adjusting the reflux ratio of the column. The C3 splitter column is preferably operated to provide an overhead product stream which has a higher mass ratio of propane to the combined amount of propene and propane than the propene starting material. Operating the C3 splitter column to provide an overhead product stream having a higher propane fraction than the propene starting material allows for increasing the propane content in the recovered propene stream, which allows the use of a smaller C3 splitter column and reduces the energy consumption for operating the column.

The C3 splitter column is preferably operated to provide a bottoms product stream which has a mass ratio of propane to the combined amount of propene and propane of at least 0.8, preferably of from 0.9 to 0.98.

In step d) of the process of the invention, the overhead product stream obtained in step c) is passed to step a).

Preferably, only a part of the recovered propene stream is fed to the C3 splitter column in step c) and the remainder is passed to step a). More preferably, from 1 to 50% by weight of the recovered propene stream is fed to the C3 splitter column and the remainder is passed to step a). The fraction of the recovered propene stream that is fed to the C3 splitter column is preferably adjusted to maintain a constant mass ratio of propane to the combined amount of propene and propane in the recovered propene stream. Feeding only a part of the recovered propene stream to the C3 splitter column allows the use of a smaller size C3 splitter column and recycling a part of the recovered propene stream directly into the epoxidation reaction increases the propane content in the reaction mixture and in the recovered propene stream, which allows the use of a C3 splitter column having fewer separation stages and operation of the column at a lower reflux ratio which saves energy.

In the process of the invention, the propene starting material may be fed to different stages.

The propene starting material may be fed directly to step a) of the process.

In a preferred embodiment, all or a part of the propene starting material is fed to the C3 splitter column of step c). Preferably, at least 20% and more preferably at least 50% of the propene starting material is fed to the C3 splitter column of step c) and the remainder is fed to step a), step b) or both. Most preferably, all propene starting material is fed to the C3 splitter column of step c). In this embodiment, the C3 splitter column is preferably operated to provide an overhead product stream which has a higher mass ratio of propane to the combined amount of propene and propane than the propene starting material. Operating the C3 splitter column to provide a vapor having a higher propane fraction than the propene starting material has the advantage that the propene starting material fed to the C3 splitter column can replace all or part of the column reflux which reduces the energy consumption of the C3 splitter column. The propene starting material is preferably fed as liquid to the C3 splitter column at a feed point above the feed point for the recovered propene stream. Feeding propene starting material to the C3 splitter column has the advantage of removing non-volatile and high boiling impurities from the propene starting material without the need for extra equipment. When the propene starting material contains no significant amount of C4+ hydrocarbons, i.e. hydrocarbons having 4 or more carbon atoms, the propene starting material is preferably fed to the uppermost tray or to the top of the uppermost packing of the C3 splitter column. This embodiment may also be used to remove C4+ hydrocarbons with the C3 splitter column bottoms product when a propene starting material comprising substantial amounts of C4+ hydrocarbons is used. A propene starting material containing significant amounts of C4+ hydrocarbons is preferably fed to the C3 splitter column at a feed point at least one theoretical stage below the column top, preferably 5 to 12 theoretical stages below the column top, in order to provide an overhead product stream with a low content of C4+ hydrocarbons.

In another preferred embodiment of the process of the invention, step b) comprises separating the recovered propene stream as an overhead product in a C3 rectifier column from a bottoms product comprising propene oxide, and all or a part of the propene starting material is fed to the C3 rectifier column. Preferably, at least 20% and more preferably at least 50% of the propene starting material is fed to the C3 rectifier column and the remainder is fed to the C3 splitter column of step c). The propene starting material is preferably fed as liquid to the C3 rectifier column at a feed point less than 10 theoretical stages from the column top. Preferably, the propene starting material is fed to the uppermost tray or to the top of the uppermost packing of the C3 rectifier column. In this embodiment, the recovered propene stream is preferably fed as a liquid to the uppermost stage of the C3 splitter column. Feeding propene starting material to the C3 rectifier column has the advantage of removing non-volatile and high boiling impurities from the propene starting material without increasing the size or the energy consumption of the C3 splitter column. This embodiment is preferably employed when a propene starting material is used which comprises only small amounts of C4+ hydrocarbons. Feeding propene starting material to the C3 rectifier column allows to further reduce the size and the energy consumption of the C3 splitter column compared to feeding propene starting material directly to the C3 splitter column.

Figure 2:
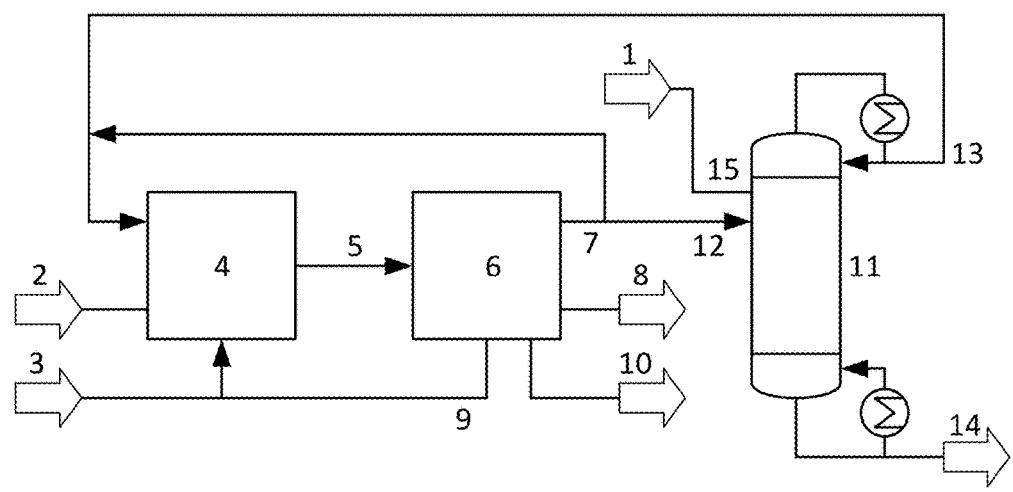
Figure 3:
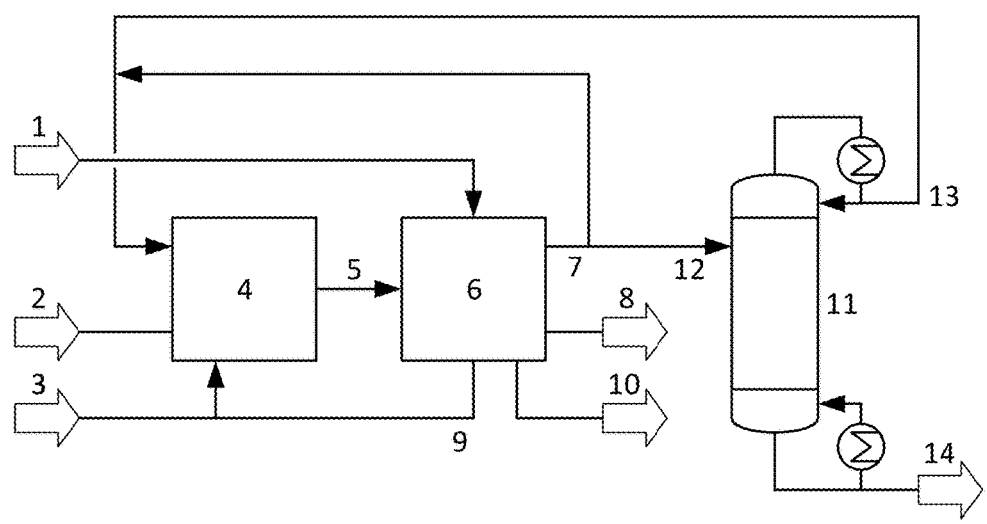

FIGS. 1 to 3 show preferred embodiments of the process of the invention.

FIG. 1 shows an embodiment where the propene starting material is fed directly to reaction step a). In this embodiment, the propene starting material (1), hydrogen peroxide (2) and a methanol solvent (3) are fed to a reaction step (4), where propene and hydrogen peroxide are reacted in the presence of an epoxidation catalyst to provide a reaction mixture (5) comprising propene oxide, non-reacted propene, propane, methanol solvent and water. This reaction mixture is separated in a separation step (6) into a recovered propene stream (7), a propene oxide product (8), a stream of recovered methanol solvent (9) which is recycled to the reaction step (4), and an aqueous stream (10). A part of the recovered propene stream (7) is fed to a C3 splitter column (11) at a feed point (12) in the upper third of the C3 splitter column (11) and the remainder of the recovered propene stream (7) is recycled to the reaction step (4). The C3 splitter column (11) provides an overhead product stream (13), depleted in propane with regard to the recovered propene stream (7), which is passed to the reaction step (4), and a bottoms product stream (14), enriched in propane with regard to the recovered propene stream (7).

The embodiment of FIG. 2 differs from the embodiment of FIG. 1 in that the propene starting material (1) is fed as liquid to a feed point (15) above the feed point (12) for the recovered propene stream instead of being fed to the reaction step (4). Feeding the propene starting material in liquid form near the top of the C3 splitter column prevents high boiling and non-volatile impurities of the propene starting material from contaminating the epoxidation catalyst and allows operation of the C3 splitter column with a low reflux ratio which saves energy. This embodiment is advantageous when the propene starting material contains significant amounts of C4+ hydrocarbons, because removal of C4+ hydrocarbons in the C3 splitter column prevents C4+ olefins contained in the propene starting material from being epoxidized in the reaction step and avoids problems in separating the propene oxide product (8) from C4+ hydrocarbons having a boiling point close to the boiling point of propene oxide.

The embodiment of FIG. 3 differs from the embodiment of FIG. 2 in that the propene starting material (1) is not fed to the C3 splitter column, but to a C3 rectifier column (not shown) of the separation step (6), in which C3 rectifier column the recovered propene stream (7) is separated as an overhead stream from a bottoms product comprising propene oxide. Feeding the propene starting material to a C3 rectifier column of separation step (6) prevents high boiling and non-volatile impurities of the propene starting material from contaminating the epoxidation catalyst, allows the use of a small sized C3 splitter column and reduces the energy consumption for propane removal. This embodiment is advantageous when the propene starting material contains only small amounts of C4+ hydrocarbons.

LIST OF REFERENCE SIGNS

1 Propene starting material
2 Hydrogen peroxide
3 Methanol solvent
4 Reaction step
5 Reaction mixture
6 Separation step
7 Recovered propene stream
8 Propene oxide product
9 Recovered methanol solvent
10 Aqueous stream
11 C3 splitter column
12 Feed point for recovered propene
13 Overhead product stream depleted in propane
14 Bottoms product stream enriched in propane
15 Feed point for propene starting material

EXAMPLES

Example 1

Propene Starting Material Fed to C3 Splitter Column

For the embodiment of FIG. 2 and an epoxidation with a titanium silicalite catalyst and a methanol solvent providing a reaction mixture containing 28.2% by weight propene and 3.7% by weight propane, the design and operation parameters of the C3 splitter column were calculated with the program Aspen Plus® of Aspen Technology varying the fraction of recovered propene fed to the C3 Splitter column. The calculations were performed for a propene starting material containing 97.5% by weight propene and 2.5% by weight propane. 32.5 t/h liquid propene starting material is fed to the top of a C3 splitter column having 101 theoretical stages operated at 2.3 MPa. The reaction step a) and the separation step b) provide a recovered propene stream of 135 t/h containing 87.2% by weight of propene and 11.5% by weight of propane. A fraction of this recovered propene stream given in table 1 is fed to the $12^{th}$ theoretical stage of the C3 splitter column (counted from column top). The remaining part of recovered propene stream is combined with the overhead product stream of the C3 Splitter column and recycled to reaction step a). A bottoms product is withdrawn from the C3 Splitter column at a rate of 0.973 t/h and the reflux ratio is adjusted to provide a propene content of 7.8% by weight in the bottoms product. Table 1 gives the feed rate of recovered propene to the C3 Splitter Column and the calculated values for the mass fraction of propane in the overhead product stream, the reflux ratio, the reboiler duty (power consumed for evaporation) and the column diameter.

TABLE 1

Calculation results for C3 splitter column with propene starting material fed to C3 splitter column

| Recovered propene fed to C3 splitter column in t/h | Mass fraction of propane in overhead product stream | Reboiler duty in kW | Reflux ratio | Column diameter in m |
|---|---|---|---|---|
| 15 | 0.037 | 11322 | 1.711 | 5.69 |
| 20 | 0.045 | 8503 | 0.822 | 4.32 |
| 25 | 0.051 | 7571 | 0.472 | 3.90 |
| 30 | 0.056 | 7226 | 0.287 | 3.75 |
| 35 | 0.061 | 7098 | 0.167 | 3.70 |
| 40 | 0.065 | 7059 | 0.078 | 3.68 |

The calculation results demonstrate that operating the C3 splitter column to provide a mass ratio of propane to the combined amount of propene and propane of at least 0.04 in the overhead product stream reduces the size of the column and the energy needed for operating the column.

Example 2

Propene Starting Material Fed to C3 Rectifier Column

The calculations of example 1 were repeated, but instead of feeding the propene starting material to the C3 splitter column, the liquid propene starting material is fed to the first theoretical stage (counted from the column top) of a C3 rectifier column of separation step b), providing as overhead product a recovered propene stream of 167 t/h containing 87.2% by weight of propene and 11.5% by weight of propane, a fraction of which is fed as liquid to the top of the C3 splitter column. Table 2 gives the feed rate of recovered propene to the C3 splitter column and the calculated values for the mass fraction of propane in the overhead product stream of the C3 splitter column, the reflux ratio, the reboiler duty (power consumed for evaporation) and the column diameter.

TABLE 2

Calculation results for C3 splitter column with propene starting material fed to C3 rectifier column

| Recovered propene fed to C3 splitter column in t/h | Mass fraction of propane in C3 splitter column overhead product stream | Reboiler duty in kW | Reflux ratio | Column diameter in m |
|---|---|---|---|---|
| 10 | 0.033 | 30192 | 39.591 | 13.79 |
| 12 | 0.048 | 17898 | 18.371 | 8.55 |
| 20 | 0.078 | 9935 | 5.039 | 4.99 |
| 30 | 0.091 | 8124 | 2.191 | 4.15 |
| 40 | 0.098 | 7441 | 1.159 | 3.85 |
| 50 | 0.102 | 7081 | 0.629 | 3.69 |
| 60 | 0.104 | 6856 | 0.306 | 3.60 |
| 70 | 0.106 | 6703 | 0.090 | 3.53 |

The calculation results demonstrate that feeding the starting material to a rectifier column of step b) may further reduce the size of the C3 splitter column and the energy needed for operating the column compared to feeding the starting material to the C3 splitter column.

Example 3

Propene Starting Material Fed to C3 Rectifier Column

The calculations of example 2 were repeated for feeding 70 t/h recovered propene stream to the C3 splitter column and providing an overhead product stream with a mass fraction of propane of 0.106, varying the feed point to the C3 splitter column. Table 3 gives the feed point in theoretical stages from the top of the C3 splitter column and the calculated values for the reflux ratio, the reboiler duty (power consumed for evaporation) and the column diameter.

TABLE 3

Calculation results for C3 splitter column with propene starting material fed to C3 rectifier column and variation of feed point to C3 splitter column

| Feed point for recovered propene in theoretical stages from column top | Reboiler duty in kW | Reflux ratio | Column diameter in m |
|---|---|---|---|
| 1 | 6703 | 0.090 | 3.53 |
| 7 | 6862 | 0.116 | 3.60 |
| 12 | 7126 | 0.160 | 3.71 |
| 20 | 7820 | 0.274 | 4.01 |

The calculation results demonstrate that for the embodiment where the propene starting material is fed to a C3 rectifier column, feeding the recovered propene to the C3 splitter column at or near the column top reduces the size of the C3 splitter column and the energy needed for operating the column.

Example 4

Propene Starting Material Fed Directly to Reaction Step a)

The calculation of example 1 was repeated for the embodiment of FIG. 1, feeding the liquid propene starting material to the epoxidation reaction and feeding the entire recovered propene stream to the $12^{th}$ theoretical stage of the C3 splitter column (counted from column top). A bottoms product is withdrawn from the C3 Splitter column at a rate of 0.968 t/h with a propene content of 1.4% by weight in the bottoms product and 131.5 t/h overhead product with a mass fraction of propane in the overhead product stream of 0.110 are recycled to the reaction step to provide the same composition of the reaction mixture as in example 1. A reboiler duty (power consumed for evaporation) of 12577 kW and a column diameter of 6.30 m were calculated for this process configuration.

Example 5 (Comparative)

Propene Starting Material Fed Directly to Reaction Step a)

The calculation of example 4 was repeated for recycling an overhead stream from the C3 splitter column having the same propane content of 2.5% by weight as the propene starting material. The lower propane content in the recycled propene stream leads to a lower mass ratio of propane to the combined amount of propene and propane in the reaction mixture and a recovered propene stream of 121 t/h containing 3.1% by weight of propane. A bottoms product is withdrawn from the C3 Splitter column at a rate of 1.285 t/h with a propene content of 5.9% by weight in the bottoms product and 119.5 t/h overhead product with a mass fraction of propane in the overhead product stream of 0.025 are recycled to the reaction step. A reboiler duty (power consumed for evaporation) of 45101 kW and a column diameter of 20.0 m were calculated for this process configuration.

Example 6

Propene Starting Material Fed Directly to Reaction Step a)

The calculation of example 4 was repeated for a propene starting material containing 95.0% by weight propene and 5.0% by weight propane, feeding 33.3 t/h liquid propene starting material to the epoxidation reaction. A bottoms product is withdrawn from the C3 Splitter column at a rate of 1.933 t/h with a propene content of 3.9% by weight in the bottoms product and 130.5 t/h overhead product with a mass fraction of propane in the overhead product stream of 0.104 are recycled to the reaction step to provide the same composition of the reaction mixture as in example 1. A reboiler duty (power consumed for evaporation) of 16552 kW and a column diameter of 8.01 m were calculated for this process configuration.

Example 7 (Comparative)

Propene Starting Material Fed Directly to Reaction Step a)

The calculation of example 5 was repeated for a propene starting material containing 95.0% by weight propene and 5.0% by weight propane, feeding 33.3 t/h liquid propene starting material to the epoxidation reaction. The lower propane content in the recycled propene stream leads to a lower mass ratio of propane to the combined amount of propene and propane in the reaction mixture and a recovered propene stream of 125 t/h containing 6.2% by weight of propane. A bottoms product is withdrawn from the C3 Splitter column at a rate of 2.120 t/h with a propene content of 3.6% by weight in the bottoms product and 122.7 t/h overhead product with a mass fraction of propane in the overhead product stream of 0.05 are recycled to the reaction step. A reboiler duty (power consumed for evaporation) of 39413 kW and a column diameter of 17.8 m were calculated for this process configuration.

Examples 4 to 7 demonstrate that operating the C3 splitter column to provide an overhead product stream which has a higher mass ratio of propane to the combined amount of propene and propane than the propene starting material reduces the size of the C3 splitter column and the energy needed for operating the column.

The invention claimed is:

1. A process for the epoxidation of propene, comprising the steps:
   a) continuously reacting propene with hydrogen peroxide in the presence of an epoxidation catalyst, using propene in molar excess to hydrogen peroxide, to provide a reaction mixture comprising propene oxide, non-reacted propene and propane;
   b) separating propene oxide and a recovered propene stream with a total content of propene and propane of more than 90% by weight from the reaction mixture obtained in step a);
   c) feeding all or a part of said recovered propene stream to a C3 splitter column for separating propene and propane and withdrawing an overhead product stream depleted in propane with regard to said recovered propene stream and a bottoms product stream enriched in propane with regard to said recovered propene stream from said column; and
   d) passing the overhead product stream obtained in step c) to step a);
   wherein a propene starting material containing propane with a mass ratio of propane to the combined amount of propene and propane of from 0.002 to 0.10 is fed to said process for the epoxidation of propene, the reaction mixture provided in step a) comprises propane with a mass ratio of propane to the combined amount of propene and propane of from 0.05 to 0.20 and the overhead product stream withdrawn from the C3 splitter column comprises propane with a mass ratio of propane to the combined amount of propene and propane of at least 0.04.

2. The process of claim 1, wherein said overhead product stream withdrawn from the C3 splitter column has a higher mass ratio of propane to the combined amount of propene and propane than said propene starting material.

3. The process of claim 1, wherein said recovered propene stream is fed to the C3 splitter column as a liquid to a feed point in the upper third of the C3 splitter column.

4. The process of claim 1, wherein all or a part of said propene starting material is fed to said C3 splitter column.

5. The process of claim 4, wherein said propene starting material is fed as liquid to said C3 splitter column at a feed point above the feed point for the recovered propene stream.

6. The process claim 1, wherein step b) comprises separating said recovered propene stream as an overhead product in a C3 rectifier column from a bottoms product comprising propene oxide, and feeding all or a part of said propene starting material to said C3 rectifier column.

7. The process of claim 6, wherein said propene starting material is fed as liquid to said C3 rectifier column at a feed point less than 10 theoretical stages from the column top.

8. The process of claim 1, wherein a part of said recovered propene stream is fed to said C3 splitter column and the remainder is passed to step a).

9. The process of claim 8, wherein the fraction of said recovered propene stream that is fed to said C3 splitter column is adjusted to maintain a constant mass ratio of propane to the combined amount of propene and propane in the recovered propene stream.

10. The process of claim 8, wherein from 1 to 50% by weight of said recovered propene stream is fed to said C3 splitter column.

11. The process of claim 1, wherein said bottoms product stream has a mass ratio of propane to the combined amount of propene and propane of at least 0.8.

12. The process of claim 1, wherein in step a) the initial molar ratio of propene to hydrogen peroxide is from 3 to 5.

13. The process of claim 1, wherein in step a) the epoxidation catalyst is a titanium zeolite containing titanium atoms on silicon lattice positions.

14. The process of claim 1, wherein in step a) the epoxidation catalyst is a homogeneous catalyst selected from heteropolytungstates and manganese chelate complexes.

15. The process of claim 14, wherein the homogeneous catalyst is a quaternary ammonium salt of a polytungstophosphate.

16. The process of claim 14, wherein the homogeneous catalyst is a manganese complex comprising at least one 1,4,7-trimethyl-1,4,7-triazacyclonane ligand.

* * * * *